United States Patent [19]

Freitas et al.

[11] Patent Number: 5,100,377

[45] Date of Patent: * Mar. 31, 1992

[54] MEDICAL EVACUATION AND IRRIGATION DEVICE

[75] Inventors: Michael W. Freitas, Irving; Wayne D. Miller, Bedford, both of Tex.

[73] Assignee: Dexide, Inc., Fort Worth, Tex.

[ * ] Notice: The portion of the term of this patent subsequent to Jul. 23, 2008 has been disclaimed.

[21] Appl. No.: 689,632

[22] Filed: Apr. 23, 1991

Related U.S. Application Data

[63] Continuation of Ser. No. 329,585, Mar. 28, 1989, Pat. No. 5,034,000.

[51] Int. Cl.⁵ .............................................. A61M 1/00
[52] U.S. Cl. ................................. 604/30; 604/33; 604/236; 604/249
[58] Field of Search ................... 604/30, 33, 35, 65, 604/236, 246, 249, 254; 137/596.2

[56] References Cited

U.S. PATENT DOCUMENTS

| | | | |
|---|---|---|---|
| 4,456,233 | 6/1984 | Ebling | 604/33 |
| 4,668,215 | 5/1987 | Allgood | 604/30 |
| 4,680,026 | 7/1987 | Weightman et al. | 604/33 |

Primary Examiner—C. Fred Rosenbaum
Assistant Examiner—Chalin Smith
Attorney, Agent, or Firm—Jackson & Walker

[57] ABSTRACT

An apparatus for selectively providing irrigation or evacuation to a patient during surgery which includes valve arrangements to prevent reflux of fluid and the drawing of irrigation fluid from a reservoir in the event the patient line becomes blocked.

1 Claim, 3 Drawing Sheets

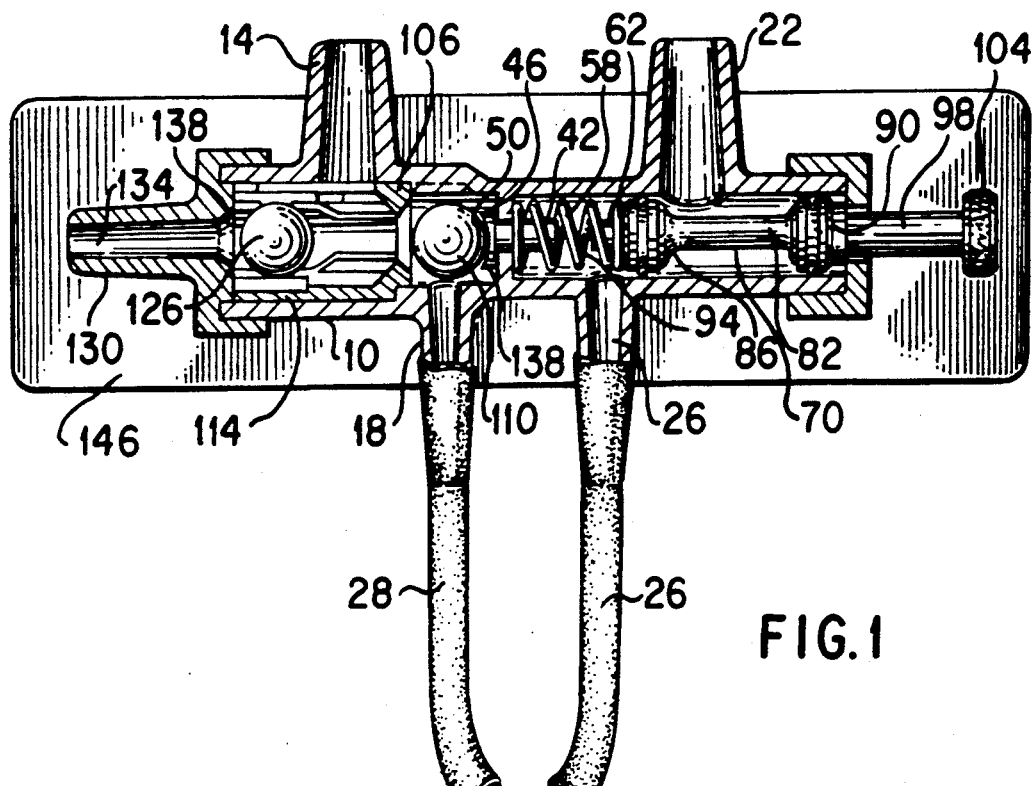
FIG. 1
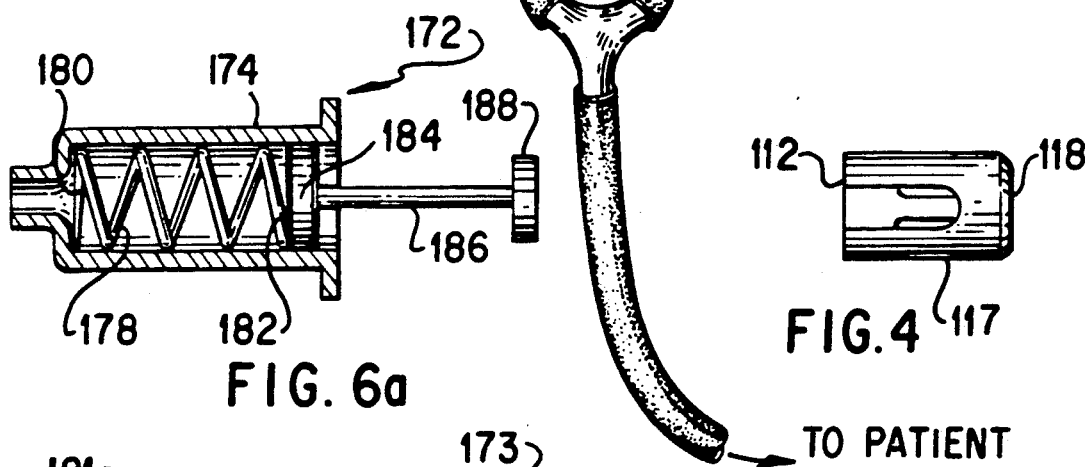
FIG. 4
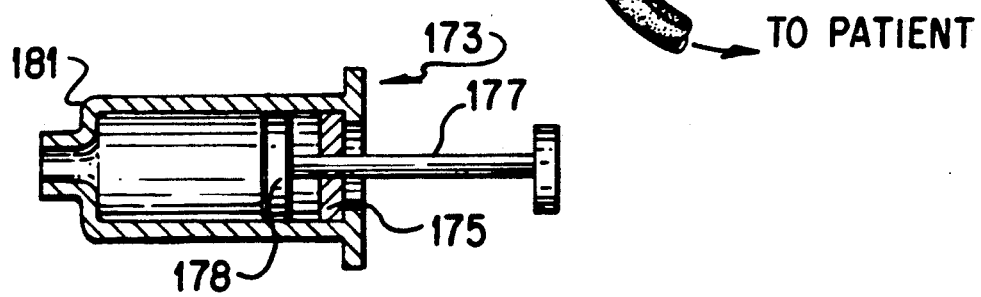
FIG. 6a
FIG. 6B

MEDICAL EVACUATION AND IRRIGATION DEVICE

This is a continuation of co-pending application Ser. No. 329,585 filed on Mar. 28, 1989, now U.S. Pat. No. 5,034,000.

TECHNICAL FIELD OF THE INVENTION

The present invention relates in general to medical devices, and more particularly relates to a device for selectively providing irrigation and evacuation to a patient during surgery.

BACKGROUND OF THE INVENTION

Development of the laparoscope and its related surgical techniques have made it possible to conduct surgery which is relatively non-invasive, without the necessity of large incisions, thus reducing trauma and the risk of infection to the patient. Laparoscopic surgery involves the use of several small incisions in the body. Through one such incision, the surgeon introduces the laparoscope, allowing the physician to insert a fiberoptic bundle that permits the surgeon to view the interior of the body. Microsurgical tools may also be inserted through the scope without impeding the physician's vision, permitting simultaneous viewing of the surgical area on a television monitor and manipulation of microsurgical tools at the surgical site. Particularly, lasers have been adapted for use with a laparoscope to conduct surgery. Often, irrigation of the surgical area is desirable. The byproducts and residue resulting from laser surgery include smoke vapors generated by the laser beam cutting the tissue as well as small pieces of tissue to be removed from the area of surgery. These by-products as well as irrigation liquids must often be removed from the patient to permit a continued unobstructed view of the surgical area. Often is it necessary to apply a vacuum to the surgical area in order to evacuate the by-products and residue of microsurgical procedures or laser surgery. A key limitation of laparoscopic surgery is the necessity of keeping the number and size of instruments introduced through the scope to a minimum.

U.S. Pat. No. 4,668,215 discloses an irrigator-evacuator control for surgical procedures which allows the selective irrigation of the area of surgery and removal of surgical residue using a remote vacuum source. It discloses a device which permits both irrigation and vacuum evacuation through a single line passed through a laparoscope or similar device to the patient. Such device eliminated the need for several individual tubes for irrigation and evacuation, reducing the size of the instruments introduced through the laparoscope. It has been found that operation of the device, wherein the device was alternatively utilized for irrigation and evacuation, may produce refluxing of by-products, residue, and irrigation solution in the patient tube if all such matter is not fully evacuated from the patient tube. Secondly, it has been found that the irrigation liquid may be drawn into the vacuum line by the force of the suction.

The present invention provides a device which permits both irrigation and vacuum evacuation of a surgical site through patient tubes passed through a laparoscope or similar device. The present invention provides a device that substantially increases the space available in the laparoscope housing for the passage of other instruments while preventing the refluxing of by-products, residue and irrigation solution through the patient tube. Finally, the present invention provides more precise control over the flow of irrigation liquid to the patient and prevents the suction of irrigation solution into the vacuum line.

SUMMARY OF THE INVENTION

The present invention provides a valve device for the convenient control and application of irrigation solution and vacuum evacuation to a patient during surgery. One embodiment of the present invention provides a valve body consisting of a passageway with a first conduit at one end to provide an inlet for irrigation solution, a second conduit at the other end to provide for connection to a source of vacuum, a third conduit disposed between the first and second conduits connected to a first patient tube through which a vacuum is applied to the surgical site, and a fourth conduit disposed between the first and third conduits connected to a second patient tube through which irrigation solution is provided. The valve body contains two passageways, one passageway being for the passage of irrigation solution and the other passageway for the application of vacuum. The valve body contains a valve which may be selectively positioned for the application of a vacuum or an irrigation solution to the patient. A vent passageway may also be provided to prevent the build up of a vacuum. The passageways and valves may be oriented in several positions. The first position connects the first and fourth conduits through the valve passageway such that an irrigation solution may flow through the fourth conduit and to the patient conduits, while sealing the second and third preventing the application of a vacuum. In this position, the vent passageway is aligned with a vent hole. In the second position, the valve passageway connects the second and third conduits such that a vacuum is applied to the surgical site through the patient tube connected to the third conduit, while the passageway to the first and fourth conduits is sealed, thus preventing the further flow of irrigation solution to the patient and preventing the reflux of irrigation solution.

In the preferred embodiment, the device is constructed from a valve body with a first end having a first conduit for connecting a line to an aspirator bulb or other suitable device, and a second end having a second conduit for connecting a line to a vacuum source, a third conduit located on the first end, between the first and second conduits for connecting a first patient tube for the application of a vacuum, a fourth conduit located on the second end, between the first and third conduits for connecting a second patient tube to provide irrigation solution to the patient, and a fifth conduit for connection to an irrigation solution source. A vent hole can be positioned on the valve body, preventing the buildup of a vacuum. Where the first and second ends of the valve body meet is a flange serving as a spring stop and a surface against which a sealing plug rests, permitting the sealing of the first and second ends of the valve body from one another. Control of the application of irrigation solution to the patient is accomplished by a valve means having a first ball located inside the first end of valve body, positioned between the first conduit and the sealing plug and which is restricted in its movement by an insert having a sealing surface. A second ball is placed in the insert and a locking connector end cap holds the components in place, providing a fifth conduit for connection to an irrigation solution source. The first end of a spring located in the second end of the valve body rests against the flange and the second end rests against the first sealing ring of a vacuum water seal assembly comprising two sealing rings separated by a connecting rod. The connecting rod extends from the first sealing ring to form an extension which is disposed within the spring. The connecting rod extends from the second sealing ring to form a plunger which extends from the end of the valve body. Attached to the plunger is a plunger button which provides for ease of operation of the plunger.

In operation of the preferred embodiment, evacuation is accomplished by pressing the plunger button which presses the plunger into the valve body which compresses the spring and pushes the first sealing ring beyond the third conduit, opening a passageway between the second and third conduits, allowing the application of an evacuation vacuum to the patient. The extension rod presses against the sealing plug which holds the first ball against the sealing surface of the insert, preventing the flow of irrigation solution through the fourth conduit to the patient. Evacuation is stopped by releasing the plunger, causing the spring to relax, restoring the seal assembly to its initial position. Irrigation is initiated by compressing an aspirator bulb connected to the first conduit. As the aspirator bulb expands, the first ball seals against the insert, closing off the passageway to the fourth conduit, preventing the flow of irrigation solution to the patient while liquid is drawn into the aspirator bulb. When the aspirator bulb is compressed again, the second ball seals against the fifth conduit while irrigation solution flows from the bulb through the fourth conduit to the surgical site.

Other embodiments are possible and a better understanding of the invention and its advantages will be apparent from the detailed description.

BRIEF DESCRIPTION OF THE DRAWINGS

Further features and advantages of the invention will become more apparent from the following and from the detailed description as illustrated in the accompanying drawings, in which:

FIG. 1 is a cross-sectional top view of the device of the present invention;

FIG. 4 is an external view of the side of the insert facing inlet 10;

FIG. 6A is a cross-sectional top view of another embodiment of the present invention employing alternative means of controlling the application of vacuum evacuation and irrigation solution;

FIG. 6B is a cross-sectional top view of another embodiment of the present invention employing alternative means of controlling the application of vacuum evacuation and irrigation solution;

DETAILED DESCRIPTION OF THE INVENTION

Figure 2:
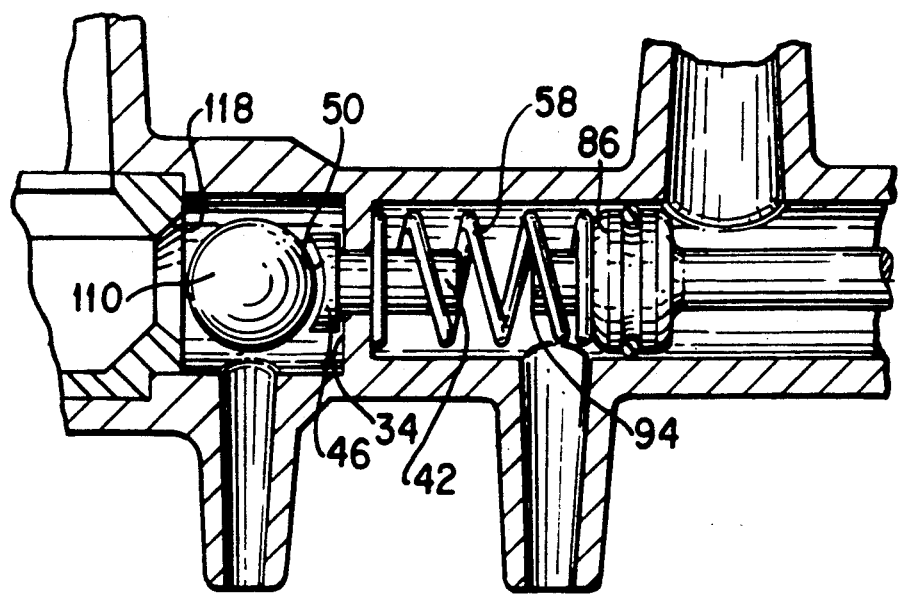
FIG. 2 is an enlarged cross-sectional top view of a portion of the vacuum seal assembly and sealing plug components.

FIG. 1 depicts one embodiment of the present invention. Illustrated is an apparatus for selectively providing irrigation and evacuation to a patient during surgery, consisting generally of a valve body 10, defining a passageway therethrough, having one end containing a first conduit 14 and a fourth conduit 18 and a second end containing a second conduit 22 and a third conduit 26. All conduits extend from the exterior to the interior of valve body 10. A first sterile patient tube 24 is connected to third conduit 26 through which a vacuum is applied to the surgical site and a second sterile patient tube 28 is connected to fourth conduit 18 through which irrigation solution flows to the patient. The sterile patient tube is passed through a laparoscope or similar device to the patient. A vent hole 30 extends from the exterior to the interior of valve body 10. Inside valve body 10, at the point where the first end and second end meet, is a flange 34, formed by the interior walls of the valve body 10 and defining a passageway therethrough, against which a sealing plug 38 rests, having a first end 42 of smaller dimension, such that first end 42 slidably engages flange 34 and having a second end 46 of larger dimension adjacent to first end 42, having an outer sealing surface 50 and an inner sealing surface 54 such that inner sealing surface 54 rests against flange 34 when sealing plug 38 is oriented in the forward position, providing a seal between the first end and the second end of valve body 10. Flange 34 also serves as a spring stop for spring 58, located in the second end of valve body 10, said spring having a first end 62 and a second end 66 such that first end 62 is seated against flange 34. Adjacent to second end 66 of spring 58 is a vacuum seal assembly 70, comprising a rod 74 having a first end and a second end, and having disposed thereon a first sealing ring 86 and a second sealing ring 90 such that first sealing ring 86 is seated against spring 58. First sealing ring 86 and second sealing ring 90 are positioned on rod 74 such that when spring 58 is in the relaxed position, vacuum seal assembly 70 is held in the normal, forward position with first sealing ring 86 positioned between second conduit 22 and third conduit 26, preventing the application of a vacuum to the surgical site. When vacuum seal assembly 70 is in the normal position, the vacuum applied through second conduit 22 draws air through vent hole 30, thus preventing the buildup of a vacuum. Although vent hole 30 is not required, it is desirable and preferred. Rod 74 extends from first sealing ring 86, forming an extension 94 which is dimensioned to pass within spring 58, such that when spring 58 is compressed when the vacuum seal assembly is selectively positioned to connect second conduit 22 and third conduit 26, extension 94 engages first end 42 of sealing plug 38. Rod 74 extends from second sealing ring 90, forming a plunger 98, which extends from the second end of valve body 10. An end cap 102 is placed over plunger 98 such that plunger 98 passes through end cap 102 and protrudes from the valve body. End cap 102 is attached to the second end of valve body 10 to hold the second end components in place. Attached to plunger 98 is plunger When evacuation is desired, plunger button 104 is pressed, pushing plunger 98 into valve body 10, causing vacuum seal assembly 70 to move in the rearward position. This causes first sealing ring 86 to compress spring 58, which is restricted in its rearward movement by flange 34, as first sealing ring 86 slides from its normal position between second conduit 22 and third conduit 26 to beyond third conduit 26, creating a passageway between second conduit 22 and third conduit 26, permitting the application of a vacuum to the patient. When first sealing ring 86 slides beyond third conduit 26, extension 94 of vacuum seal assembly 70 engages first end 42 of sealing plug 38, causing sealing plug 38 to move rearwardly, such that outer sealing surface 50 of sealing plug 38 engages first ball 110, such that first ball 110 seals against sealing surface 118 of insert 114. This causes the chamber formed by first conduit 14, fifth conduit 134 and first ball 110 to be sealed from the remainder of valve body 10 and stops the flow of irrigation solution through fourth conduit 18 to the patient during evacuation of the surgical site and prevents the refluxing of irrigation solution and evacuated debris in the patient tube. Second sealing ring 90 seals second end of valve body 10, preventing exposure of the vacuum to the atmosphere by sealing off vent hole 30, thus avoiding a corresponding reduction in efficiency of the vacuum. When evacuation is complete, plunger button 104 is released. Spring 58 relaxes, causing vacuum seal assembly 70 to move in the forward direction until it returns to its normal position such that first sealing ring 86 is positioned between second conduit 22 and third conduit 26, closing the passageway between the vacuum source and the patient. Accordingly, second sealing ring 90, plunger 98 and plunger button 104 will return to their normal positions and a passageway is again formed between second conduit 22 and vent hole 30. Vent hole 30 is not required; however, it is desirable in order to prevent vacuum surges when vacuum seal assembly 70 is actuated in the evacuation position. Vent hole 30 is not necessary if other means are used to control vacuum surge.

FIG. 4 illustrates insert 114 having sealing surface 118 against which first ball 116 seals. The cutout provided in insert 114 is aligned with first conduit 12 so that first conduit 12 is not blocked by insert 56. Insert 114 is not required; however, it is desirable and preferred to allow the unimpeded flow of irrigation solution to the aspirator bulb connected to first conduit 14 as the irrigation bulb is filled. Insert 114 is not necessary if other means are employed to insure the unimpeded flow of irrigation solution to first conduit 14.

Figure 5:
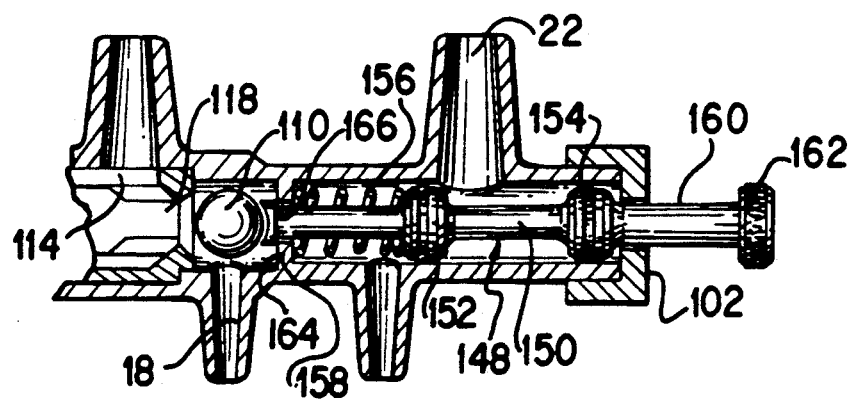
FIG. 5 is a cross-sectional top view of another embodiment of the present invention wherein the vacuum seal assembly and flange seal are dimensioned as one component.

It will be clear to those skilled in the art that it is not necessary to provide the separate components of sealing plug 38 and extension 94. The use of separate components is not required; however, it is desirable and preferred because such arrangement affords ease of construction and allows for less demanding tolerances. Alternatively, sealing plug 38 and extension 94 may form part of the vacuum seal assembly if so dimensioned. FIG. 5 shows another embodiment of the present invention. Illustrated is a vacuum seal assembly generally identified as 148, comprising a rod 150 having a first end and a second end, and having disposed thereon a first sealing ring 152 and a second sealing ring 154, such that first sealing ring 152 is seated against first end of a spring 156, having a second end which is seated against and is restricted in its rearward movement by flange 158, which is formed by the interior walls of valve body 10 at the point where the first end and second end of valve body 10 meet. First sealing ring 152 and second sealing ring 154 are positioned on rod 150 such that when spring 156 is in the relaxed position, vacuum seal assembly 148 is held in the normal forward position with first sealing ring 152 positioned between second conduit 22 and third conduit 26. Rod 150 extends from first sealing ring 152 and is dimensioned to pass within spring 156 and to pass within and slidably engage flange 158. Rod 150 extends from second sealing ring 154 to form a plunger 160, which extends from the second end of valve body 10. End cap 102 is placed over plunger 196 such that plunger 160 passes through end cap 102 and protrudes from the second end of valve body 10. Attached to plunger 160 is plunger button 162 which provides for ease of operation of plunger 160 to actuate vacuum seal assembly 148. Attached to the end of rod 74 is flange seal 164, having an inner sealing surface 190 and an outer sealing surface 168, located in the first end of valve body 10 and dimensioned such that when vacuum seal assembly 148 is in the normal forward position, inner sealing surface 166 of flange seal 164 rests against flange 158, providing a seal between the first end and second end of valve body 10.

When evacuation is desired, plunger button 162 is pressed, pushing plunger 160 into valve body 10, causing vacuum seal assembly 148 to move in the rearward, actuated position, causing first sealing ring 152 to compress spring 156 as first sealing ring 152 slides from its normal position between second conduit 22 and third conduit 26 to beyond third conduit 26, creating a passageway which permits the application of a vacuum to the patient. When first sealing ring 152 moves into the actuated position, flange seal 164 is positioned in the rearward position such that outer sealing surface 168 of flange seal 164 engages first ball 110, such that first ball 110 seals against sealing surface 118 of insert 114, stopping the flow of irrigation solution through fourth conduit 18 to the patient during evacuation of the surgical site and preventing the refluxing of irrigation solution and evacuated debris in the patient tube.

Other components can be substituted for the components illustrated in FIGS. 1-4. The operation of the apparatus illustrated in FIGS. 1-4 is accomplished utilizing an aspirator bulb connected to first conduit 14 to provide the necessary force to draw irrigation solution into the valve body from an irrigation solution source and to expel the irrigation fluid through fourth conduit 18 through patient tube 28 and to the patient. Although the use of an aspirator bulb is not required, it is desirable and preferred. The use of an aspirator bulb is not necessary if other components and/or means are provided to accomplish the drawing and expelling of irrigation solution through the conduits for the selective application of irrigation solution to the surgical site.

FIG. 6 illustrates one alternative arrangement which can be substituted for the aspirator bulb utilized with first conduit 14 in FIGS. 1-4. Illustrated is a spring return syringe generally identified as 172, comprising a syringe body 174, having a first end and a second end, such that the diameter of the first end reduces in dimension and is connected to first conduit 14 and the second end holds the spring return syringe components in place and forms a syringe grip 176 to facilitate the easy operation of the spring return syringe device. Contained within syringe body 174 is a syringe spring 178, having a first end 180 and a second end 182 such that first end 180 abuts and is positioned against the first end of sybutton 104 which provides for ease of operation of plunger 98 to actuate vacuum seal assembly 70.

Located inside the first end of valve body 10, between first conduit 14 and fourth conduit 18, is an insert stop 106. A first ball 110 is inserted in the first end of valve body 10 and is freely movable between the insert stop 106 and outer sealing surface 50 of sealing plug 38 when inner sealing surface 54 of sealing plug 38 rests against flange 34. An insert 114 having a sealing surface 118 and a nonsealing end 112 is positioned in the first end of the valve body 10 such that insert 114 is restricted in its forward movement by insert stop 106 and such that sealing surface 118 of insert 114 faces first ball 110. A second ball 126 is located in insert 114 and is freely movable between nonsealing end 122 of insert 114 and the first end of valve body 10. A connector end cap 130 is attached to the first end of valve body 10 to hold the first end components in place, forming a fifth conduit 134 and forming an internal sealing surface 138 for second ball 126.

FIG. 2 is an enlarged cross-sectional top view of the device of the present invention depicting the arrangement of components of the sealing means of the present invention. comprising: first sealing ring 86, extension 94, spring 58, sealing plug 38, having first end 42 and second end 46, having an outer sealing surface 50 and inner sealing surface 54, first ball 110 and sealing surface 118. This arrangement of individual components is not required; however, it is desirable and has been found preferable because such arrangement affords ease of construction and allows for less demanding tolerances. This arrangement of components is not necessary if other components and/or means are provided to accomplish the selective opening and closing of passageways connecting the conduits for the selective application of irrigation solution and evacuation to a surgical site.

Figure 3:
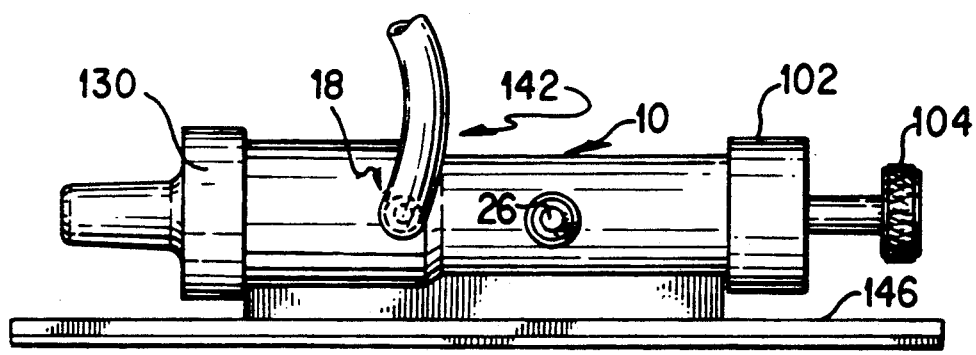
FIG. 3 is an external side view of the device of the present invention.

FIG. 3 shows an exterior side view of the device of the present invention. A grip 142 and a stand 146 are attached to the exterior of the device. Stand 146 is used to facilitate securing the device to a convenient fixed object and grip 146 facilitates the easy operation of plunger 98 when plunger button 104 is pressed.

The present invention provides a device which permits both irrigation and vacuum evacuation through a patient tube which passes through a laparoscope or similar device to the surgical site. The present invention provides a device that minimizes the space required to accomplish irrigation and evacuation in laparoscopic procedures, thereby substantially increasing the space available in the laparoscope housing for the passage of other instruments while preventing the refluxing of by-products through the patient tube. In operation, only two controls, plunger button 104 and preferably an aspirator bulb or similar device connected to first conduit 14 need be manipulated to irrigate and evacuate the surgical area. Reflux within the patient tube of tissue, surgical by-products and irrigation solution is avoided because the device of the invention utilizes two separate conduits to apply irrigation solution and evacuation vacuum to the surgical area, having a first patient tube 24 connected to third conduit 18 through which a vacuum is applied to the surgical site and a second patient tube 28 connected to fourth conduit 14 through which irrigation solution is delivered to the patient. The present invention provides more precise control over the flow of irrigation fluid to the patient, preventing the source of irrigation fluid from being drained. The irrigation evacuation device of the invention prevents the inadvertent flow of irrigation solution to the patient during evacuation of the surgical site, thereby preventing reflux of irrigation solution and by-products in the patient tube and thus, allowing the source of irrigation fluid to be elevated at any position with respect to the device. Utilization of separate conduits to apply irrigation solution and evacuation vacuum assures that irrigation solution is not inadvertently drawn back into the patient tube during evacuation; thereby, the irrigation solution remains uncontaminated. Furthermore, in the event the patient tube becomes clogged with debris during evacuation of the surgical site, the utilization of two conduits easily permits the clearing of the patient tube.

The simplicity and ease of operation of the present invention is apparent from a consideration of FIGS. 1-4. Vacuum tubing is attached at one end to a vacuum source and at the other end to second conduit 22. Sterile tubing is connected at one end to an irrigation solution reservoir source and at the other end to fifth conduit 134. An aspirator bulb or other suitable device is connected to first conduit 14. The aspirator bulb is compressed and released. As the aspirator bulb expands, a vacuum is created, causing first ball 110 to seal against sealing surface 118 of insert 114, forming a seal between the chamber formed by the first end of valve body 10, first conduit 14 and connector end cap 130 from fourth conduit 18 leading to the patient, which prevents the flow of irrigation solution to the patient. The vacuum created by the expansion of the aspirator bulb pulls second ball 126 against nonsealing end 122 of insert 114 and draws liquid from the irrigation source, through fifth conduit 134 and through the channels in insert 114, around second ball 126, through the passageway formed by first conduit 14, first ball 110 and fifth conduit 134 and into the aspirator bulb. Irrigation solution does not fill beyond sealing surface 118 of insert 114, because first ball 110 forms a seal which is not broken until the aspirator bulb is again compressed.

When irrigation is desired, the operator compresses the aspirator bulb, creating pressure which forces second ball 126 against the sealing surface of connector end cap 130, preventing irrigation solution from being transferred back into the irrigation solution reservoir source. The pressure created when the aspirator bulb is compressed causes first ball 110 to press against outer sealing surface 50 of sealing plug 38, forcing sealing plug 38 in the forward position, such that inner sealing surface 54 rests against flange 34, sealing the chamber created by first ball 110, second ball 126, first conduit 14 and fourth conduit 18 from the remainder of valve body 10. As the operator compresses the aspirator bulb, irrigation liquid is forced from the aspirator bulb, through first conduit 14, around first ball 110 into fourth conduit 18 and through the patient tube to the irrigation site. When irrigation is complete, the aspirator bulb is released. As the aspirator bulb expands, irrigation solution is once again drawn from the irrigation solution reservoir as first ball 110 is sealed against sealing end 118 of insert 114 and second ball 126 is pulled against nonsealing end 122 of insert 114, filling the chamber formed by the valve body 10, first ball 110, first conduit 14, and connector end cap 130. Again, irrigation solution does not fill beyond sealing surface 118 of insert 114, since first ball 110 forms a seal which is not broken until the aspirator bulb is again compressed.

ringe body 174, at the point where its diameter reduces in dimension. Second end 182 of syringe spring 178 is disposed within syringe body 174 and abuts the first end of a syringe seal 184, having a second end from which a syringe plunger 186 extends. Syringe plunger extends from the second end of syringe body 174, said second end holding the spring return syringe component in place. Adjacent to syringe plunger 186 is syringe plunger button 188, which facilitates the easy operation of spring return syringe 172. In operation, syringe plunger button 188 is depressed, pushing syringe plunger 186 into syringe body 174 and compressing syringe spring 178. When syringe plunger button 188 is released, syringe spring 178 returns to its relaxed position creating a vacuum, causing first ball 110 to seal against sealing surface 118 of insert 114, forming a seal between the chamber formed by the first end of valve body 10, first conduit 14 and connector end cap 130 from fourth conduit 18, preventing the flow of irrigation solution to the patient. The vacuum created pulls second ball 126 against nonsealing end 122 of insert 114, and draws liquid from the irrigation source, through fifth conduit 134 and through the channels in insert 114, around second ball 126, and into spring return syringe 172. In this manner, a quantitative amount of irrigation solution may be precisely drawn into the syringe. Irrigation solution does not fill beyond sealing surface 118 of insert 114 because first ball 110 forms a seal which is not broken until syringe plunger button 188 is compressed.

When irrigation of a surgical site is desired, the operator presses surgical plunger button 188, pushing syringe plunger 186 into syringe body 174, creating pressure which forces second ball 126 against the sealing surface of connector end cap 130, preventing irrigation solution from being transferred back into the irrigation solution reservoir source. The pressure created causes first ball 110 to press against outer sealing surface 50 of sealing plug 38, forcing it in the forward position such that sealing surface 54 rests against flange 34. As the operator compresses the syringe plunger 186, a precise amount of irrigation liquid is forced from syringe body 174, to fourth conduit 18, through the patient tube and to the surgical irrigation site. When irrigation is complete, syringe plunger button 188 is released and syringe spring 178 returns to its relaxed position, creating a vacuum which once again causes irrigation solution to be drawn into the syringe body 174.

Figure 7:
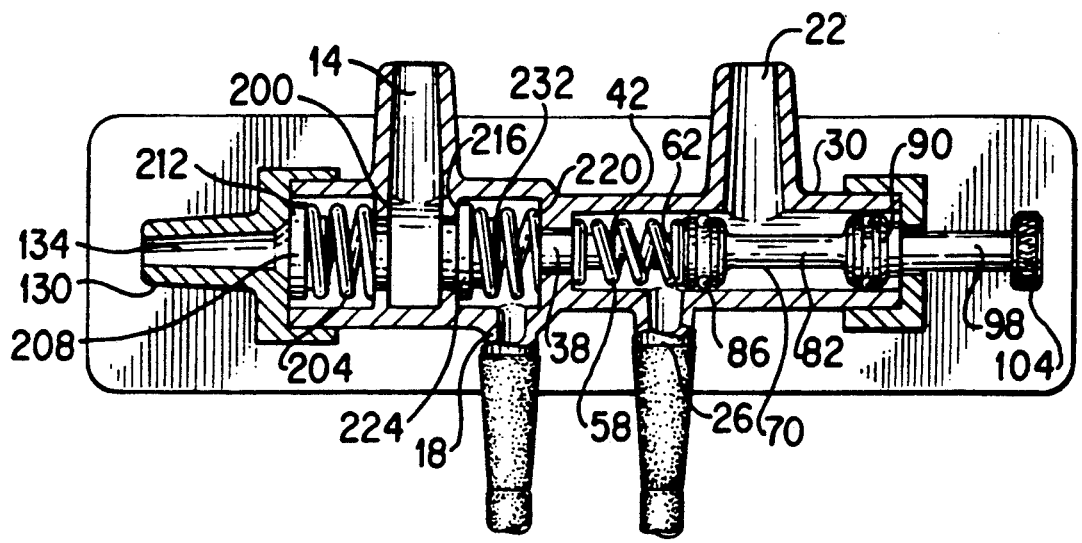
FIG. 7 is a cross-sectional top view of another embodiment of the present invention using an alternative sealing arrangement to seal the first conduit and fourth conduit.

FIG. 7 illustrates one alternative arrangement which can be substituted for the ball seals utilized in the first end of valve body 10 as illustrated in FIG. 1. In FIG. 7, four ribs 200 are located in the first end of valve body 10 between first conduit 14 and fifth conduit 134. Illustrated is a first sealing assembly, comprising a first spring 204, having a first end and a second end, such that the first end is seated against four ribs 200 and the second end abuts a first seal 208, such that when said first spring is in the relaxed position, first seal 208 rests against the inside sealing surface 212 of connector end cap 130 which forms fifth conduit 134. Located between first conduit 14 and fourth conduit 18 is sealing flange 216, formed by the interior walls of valve body 10 and against which a second sealing assembly abuts. The second sealing assembly comprises a second spring 220, having a first end and a second end such that the first end is seated against flange 34 and the second end engages a second seal 224, such that when second spring 220 is in the relaxed position, second seal 224 rests against sealing flange 216, sealing first conduit 14 from fourth conduit 18. Second seal 224 has a first end 228 of larger dimension and a second end 232 of smaller dimension adjacent thereto, such that second end 232 is dimensioned to pass within second spring 220, such that when second seal 224 is in the forward position, second end 232 engages sealing plug 38, creating a seal between sealing plug 38 and flange 34. Other embodiments of a syringe may be used, for example, in FIG. 6B, a syringe 173 with a plug 175 at the second end through which the plunger 177 passes. In this type of syringe depressing, the plunger results in creating a vacuum as the syringe seal member 179 moves away from the plug 175 and upon release the syringe plunger 177 will return to its original position, thereby drawing liquid in the syringe body 181.

In operation, the aspirator bulb connected to first conduit 14 is compressed. As the aspirator bulb expands, a vacuum is created, pulling first seal 208 away from inside sealing surface 212, compressing first spring 204, and causing irrigation solution to be drawn through fifth conduit 134, through the channels created by ribs 200, through the passageway formed by first conduit 14, second seal 224 and fifth conduit 134 and into the aspirator bulb. Irrigation solution does not fill beyond sealing flange 216 because second seal 220 is held against sealing flange 216, forming a seal which is not broken until the aspirator bulb is again compressed. When the aspirator bulb is full and suctioning ceases, first spring 204 forces first seal 208 against inside sealing surface 212 of fifth conduit 134 to prevent irrigation solution from flowing back into the irrigation solution source.

When irrigation is desired, the operator compresses the aspirator bulb, creating pressure which forces second seal 224 to move in the forward direction, breaking the seal between sealing flange 216 and first end 228 of second seal 224 and compressing second spring 220. As second seal 224 moves in the forward direction, second end 232 of second seal 224 engages sealing plug 38, forcing sealing plug 38 in the forward position such that inner sealing surface 54 rests against flange 34, creating a seal between inner sealing surface 54 of sealing plug 38 and flange 34, such that the chamber created by first conduit 14, sealing plug 38, fourth conduit 18 and first seal 208 is sealed from the remainder of valve body 10. As the operator compresses the aspirator bulb, irrigation solution is forced from the aspirator bulb, through first conduit 14, through fourth conduit 18 and through second patient tube to the irrigation site. When the aspirator bulb is fully compressed, the flow of liquid ceases and second spring 220 relaxes, forcing second seal 224 to its initial position wherein first end 228 is seated against sealing flange 216 and the cycle can be repeated.

Figure 8:
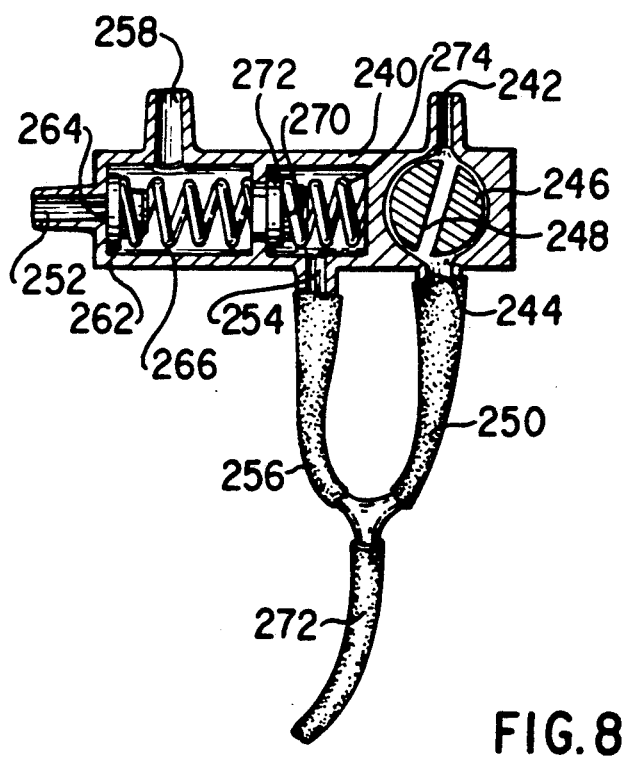
FIG. 8 is a cross-sectional top view of another embodiment of the present invention wherein irrigation fluid is drawn into and expelled from the valve body via a spring return syringe.

Another embodiment of the present invention is illustrated in cross section in FIG. 8. In FIG. 8, a valve body 240 is shown which is provided with two distinct passageways, a vacuum passageway having a first end 242, providing a conduit formed by the walls of valve body 240 which may be connected to a vacuum source and a second end 244, forming a conduit which leads to the patient. Disposed between first end 242 and second end 244 is rotating valve member 246 which rotatably engages the interior walls of valve body 240. Rotating valve member 246 contains a valve passageway 248, such that when rotating valve member 246 is selectively positioned a passageway is formed connecting first end 242 and second end 244, such that a vacuum may be selectively applied to the patient through patient tube 250 connected to the conduit formed by second end 244. When valve member 248 is rotated, the vacuum passageway can be completely open or the passageway can be closed, thus preventing the application of a vacuum to the patient. An irrigation solution passageway is provided, having an inlet 252, which may be connected to a source of irrigation fluid and having an outlet 254, which may be connected to a first patient tube 256 leading to the patient. A conduit 258 is provided, which is in communication with the irrigation solution passageway between inlet 252 and outlet 254. An aspirator bulb or other suitable device may be attached to conduit 258 to provide a means to draw liquid into the irrigation solution passageway and to expel irrigant from the irrigation solution passageway. Positioned adjacent to inlet 252 is a first check valve 260, comprising a seal 262, having a first end and a second end, such that said first end abuts sealing surface 264 formed by the interior walls of valve body 240 and said second end abuts the first end of a spring 266, said spring having a second end which abuts flange 268 formed by the interior walls of valve body 240 and is disposed intermediate of conduit 258 and second outlet end 254. Spring 266 is of sufficient tension to permit irrigant to be drawn into the irrigation solution passageway by a force exerted through conduit 256, such as by an expanding aspirator bulb. A second check valve 268 is provided, comprising a seal 272, having a first end and a second end such that said first end abuts flange 268 and said second end abuts the first end of a spring 274 which forces seal 272 against flange 268 when spring 266 is in the normal relaxed position, forming a seal between conduit 258 and outlet 254. First patient tube 250 and second patient tube 256 join to form a combined patient tube 276, which may pass through a laparoscope or other device to the patient. In operation, should patient tube 276 become clogged or plugged, a vacuum will be drawn through patient tubes 250 and 256, evacuating second patient tube 256 of any irrigant but not drawing any irrigant from beyond the point of second check valve 270, because spring 266 is of sufficient tension to hold seal 272 tightly against flange 268 while a vacuum is applied through second patient tube 256. When irrigation is desired, second check valve 270 allows the passage of irrigation solution through outlet 252 under a force exerted through conduit 258, such as by compression of an aspirator bulb. In operation, an aspirator bulb attached to conduit 258 is compressed. As the bulb inflates, the vacuum created is of sufficient force to overcome the tension of spring 266 permitting the passage of irrigating fluid through inlet 264, around seal 262, filling the aspirator bulb. The vacuum created also holds seal 272 of second check valve 270 against flange 268, preventing the flow of irrigation solution to the patient until the aspirator bulb is again compressed. Once the aspirator bulb is full, suction ceases and the tension in spring 266 causes seal 262 to seal against sealing surface 264, preventing the flow of irrigation solution back into the irrigation solution source. When irrigation is desired, the aspirator bulb is again compressed. The force exerted by the irrigation fluid expelled by the aspirator bulb is sufficient to overcome the tension exerted by spring 274, breaking the seal between seal 272 and flange 268 and permitting the flow of fluid through outlet 254 and patient tube 256 to the surgical site. In normal operation, rotating valve member 246 will be positioned such that first end 242 and second end 244 are not in communication, preventing the application of a vacuum to patient tubes 250 and 256. Thereafter, rotating valve member 246 may be rotatably positioned to align valve passageway 248 with first and second ends 242 and 244 to allow evacuation of fluid and debris from the surgical site.

One skilled in the art will recognized at once it would be possible to construct the present invention from a variety of materials and that the materials should be sterilizable. The present invention can be constructed so that it is either reusable or disposable after one use. Suitable materials include stainless steel and a wide variety of plastics commonly used in the medical field. Sealing rings may be made of any suitable material which is slidable in the passageway defined by the valve body. For example, they may be constructed of a solid disc dimensioned with a groove to accept an 0-ring, thus creating a slidable seal.

While the preferred embodiment of the present has been described in detail, and shown in the accompanying drawings, it will be evident that various further modifications and uses not illustrated are possible without departing from the scope of the invention.

I claim:

1. An apparatus for the selective alternating of the passage of an irrigation fluid and the application of an evacuation vacuum through an endoscopic surgical instrument insertable into a patient, comprising:
    a body defining at least two passage ways therethrough;
    a first valve means located in the first passage way of said valve body to permit the selective opening and closing of a passageway to one of irrigation fluid and evacuation vacuum; and
    a second valve means to permit the selective opening and closing of a passage way for the other of irrigation fluid and evacuation vacuum.

* * * * *